(12) United States Patent
Peters et al.

(10) Patent No.: US 7,314,870 B2
(45) Date of Patent: Jan. 1, 2008

(54) COMPOUNDS, THEIR PREPARATION AND USE

(75) Inventors: Dan Peters, Ballerup (DK); Gunnar M. Olsen, Ballerup (DK); Elsebet Ostergaard Nielsen, Ballerup (DK); Philip K. Ahring, Ballerup (DK); Tino Dyhring Jorgensen, Ballerup (DK)

(73) Assignee: Neurosearch A/S, Ballerup (DK)

( * ) Notice: Subject to any disclaimer, the term of this patent is extended or adjusted under 35 U.S.C. 154(b) by 337 days.

(21) Appl. No.: 10/482,363

(22) PCT Filed: Jul. 2, 2002

(86) PCT No.: PCT/DK02/00460

§ 371 (c)(1),
(2), (4) Date: Dec. 30, 2003

(87) PCT Pub. No.: WO03/004493

PCT Pub. Date: Jan. 16, 2003

(65) Prior Publication Data

US 2004/0180877 A1    Sep. 16, 2004

(30) Foreign Application Priority Data

Jul. 6, 2001    (DK) .............................. 2001 01064

(51) Int. Cl.
*A61P 25/28*    (2006.01)
*A61K 31/435*    (2006.01)
*A61K 31/495*    (2006.01)
*C07D 487/04*    (2006.01)
*C07D 453/02*    (2006.01)

(52) U.S. Cl. ................. 514/214.03; 514/299; 514/304; 514/414; 540/477; 540/585; 546/112; 546/126

(58) Field of Classification Search ........... 514/214.03, 514/299, 304, 414; 540/477, 585; 546/112, 546/126
See application file for complete search history.

(56) References Cited

FOREIGN PATENT DOCUMENTS

| WO | WO 92/03433 A | 3/1992 |
|---|---|---|
| WO | WO 93/23395 A | 11/1993 |
| WO | WO 00/64885 A | 11/2000 |
| WO | WO 00/66586 A | 11/2000 |
| WO | WO 01/36417 A | 5/2001 |
| WO | WO 01/92261 A | 12/2001 |
| WO | WO 02/44176 A | 6/2002 |

OTHER PUBLICATIONS

Nilsson, B. M. et al., Journal of Medicinal Chemistry, American Chemical Society. Washington, U.S. vol. 38, No. 3, 1995, pp. 473-487.

*Primary Examiner*—Brenda Coleman
(74) *Attorney, Agent, or Firm*—Birch, Stewart, Kolasch & Birch, LLP

(57) ABSTRACT

The present invention relates to novel compounds that are found to be cholinergic ligands at the nicotinic acetylcholine receptors and modulators of the monoamine receptors and transporters.

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

10 Claims, No Drawings

COMPOUNDS, THEIR PREPARATION AND USE

This application is a national stage entry under 35 U.S.C. §371 of PCT/DKO2/00460, filed Jul. 2, 2002.

TECHNICAL FIELD

The present invention relates to novel compounds that are found to be cholinergic ligands at the nicotinic acetylcholine receptors and modulators of the monoamine receptors and transporters.

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

BACKGROUND ART

The endogenous cholinergic neurotransmitter, acetylcholine, exert its biological effect via two types of cholinergic receptors, the muscarinic Acetyl Choline Receptors (mAChR) and the nicotinic Acetyl Choline Receptors (nAChR).

As it is well established that muscarinic acetylcholine receptors dominate quantitatively over nicotinic acetylcholine receptors in the brain area important to memory and cognition, and much research aimed at the development of agents for the treatment of memory related disorders have focused on the synthesis of muscarinic acetylcholine receptor modulators.

Recently, however, an interest in the development of nAChR modulators has emerged. Several diseases are associated with degeneration of the cholinergic system i.e. senile dementia of the Alzheimer type, vascular dementia and cognitive impairment due to the organic brain damage disease related directly to alcoholism. Indeed several CNS disorders can be attributed to a cholinergic deficiency, a dopaminergic deficiency, an adrenergic deficiency or a serotonergic deficiency.

SUMMARY OF THE INVENTION

The present invention is devoted to the provision novel modulators of the nicotinic and/or of the monoamine receptors, which modulators are useful for the treatment of diseases or disorders related to the cholinergic receptors, and in particular the nicotinic acetylcholine receptor (nAChR), the monoamine receptors 5-HTR, DAR and NER, and the biogenic amine transporters for 5-HT, DA and NE.

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

The compounds of the invention may also be useful as diagnostic tools or monitoring agents in various diagnostic methods, and in particular for in vivo receptor imaging (neuroimaging), and they may be used in labelled or unlabelled form.

In its first aspect the invention provides novel chemical substances represented by the general Formula I

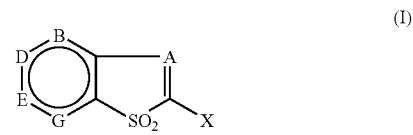

(I)

any of its enantiomers or any mixture of enantiomers, or a pharmaceutically-acceptable addition salt thereof, wherein A, B, D, E and G, independently of each another, represent a carbon (C) or a nitrogen (N) atom, constituting an-aromatic ring system; and X represents a group of Formula II

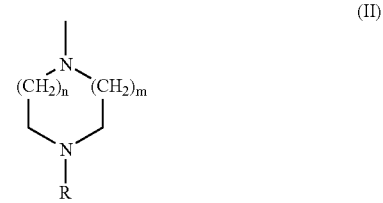

(II)

a group of Formula III

(III)

a group of Formula IV

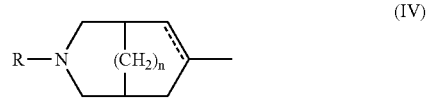

(IV)

a group of Formula V

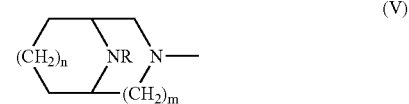

(V)

a group of Formula VI

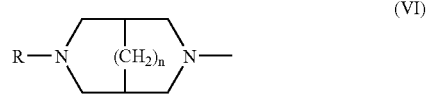

(VI)

a group of Formula VII

(VII)

or a group of Formula VIII

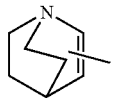
(VIII)

in which formulas = represents a single or a double bond (an optionally double bond); n is 0, 1, 2 or 3; m is 1, 2 or 3; and R represents hydrogen, alkyl, alkenyl, alkynyl, cycloalkyl, cycloalkylalkyl, aryl or aralkyl.

In another aspect the invention provides pharmaceutical compositions comprising a therapeutically effective amount of the chemical substance of the invention, any of its enantiomers or any mixture of its enantiomers, or a pharmaceutically-acceptable addition salt thereof, together with at least one pharmaceutically-acceptable carrier or diluent.

In yet another aspect the invention relates to the use of the chemical substance of the invention for the treatment, prevention or alleviation of a disease or a disorder or a condition, which is responsive to modulation of cholinergic receptors and/or monoamine receptors.

In still another aspect the invention provides methods of treatment, prevention or alleviation of diseases, disorders or conditions of a living animal body, which disease or disorder is responsive to modulation of cholinergic receptors and/or monoamine receptors, which method comprises the step of administering to such a living animal body, including a human, in need thereof a therapeutically effective amount of the chemical substance of the invention.

Other objects of the invention will be apparent to the person skilled in the art from the following detailed description and examples.

DETAILED DISCLOSURE OF THE INVENTION

In its first aspect the present invention provides novel chemical substances represented by the general Formula I

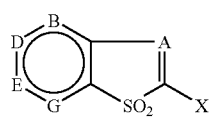
(I)

any of its enantiomers or any mixture of enantiomers, or a pharmaceutically-acceptable addition salt thereof, wherein A, B, D, E and G, independently of each another, represent a carbon (C) or a nitrogen (N) atom, and wherein no more than two of B, D, E and G represent nitrogen atoms while the remainder of B, D, E and G represent carbon atoms, thereby constituting an aromatic ring system; and X represents a group of Formula II

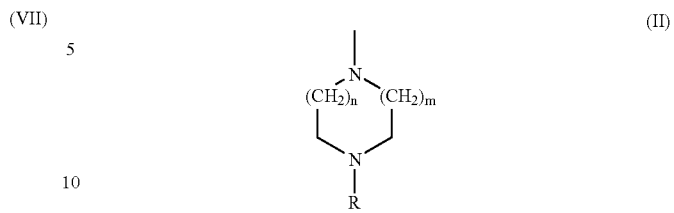
(II)

a group of Formula III

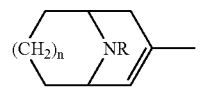
(III)

a group of Formula IV

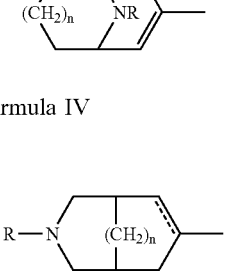
(IV)

a group of Formula V

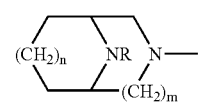
(V)

a group of Formula VI

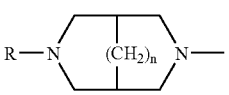
(VI)

a group of Formula VII

(VII)

or a group of Formula VIII

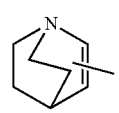
(VIII)

in which formulas
= represents a single or a double bond (an optionally double bond);

n is 0, 1, 2 or 3;
m is 1, 2 or 3; and
R represents hydrogen, alkyl, alkenyl, alkynyl, cycloalkyl, cycloalkylalkyl, aryl or aralkyl.

In a preferred embodiment, the chemical substance of the invention is a benzo[b]thiophene derivative of Formula IA

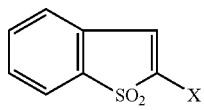

(IA)

a benzo[b]thiazole derivative of Formula IB

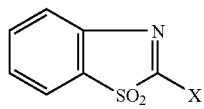

(IB)

a thienopyridine derivative of Formula IC

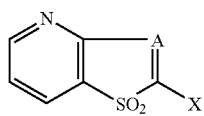

(IC)

a thienopyridine derivative of Formula ID

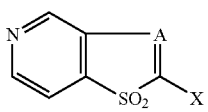

(ID)

a thienopyridine derivative of Formula IE

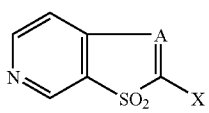

(IE)

or a thienopyridine derivative of Formula IF

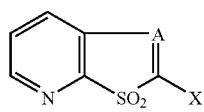

(IF)

in which formulas
A and X are as defined above.

In a more preferred embodiment, the chemical substance of the invention is a benzo[b]thiophene derivative of Formula IA, wherein X represents a group of Formula II, wherein n is 0, 1 or 2; m is 1, 2 or 3; and R represents hydrogen, alkyl, or aralkyl.

In a most preferred embodiment the benzo[b]thiophene derivative of the invention is
(±) 1-(2-Benzo[b]thiophenyl-1,1-dioxide)-imidazolidine;
(±) 1-(2-Benzo[b]thiophenyl-1,1-dioxide)-3-methyl-imidazolidine;
(±) 1-(2-Benzo[b]thiophenyl-1,1-dioxide)-1,3-diazacyclohexane;
(±) 1-(2-Benzo[b]thiophenyl-1,1-dioxide)-3-methyl-1,3-diazacyclohexane;
(±) 1-(2-Benzo[b]thiophenyl-1,1-dioxide)-piperazine;
(±) 1-(2-Benzo[b]thiophenyl-1,1-dioxide)-4-methyl-piperazine;
(±) 1-(2-Benzo[b]thiophenyl-1,1-dioxide)-4-ethyl-piperazine;
(±) 1-(2-Benzo[b]thiophenyl-1,1-dioxide)-4-benzyl-piperazine;
(±) 1-(2-Benzo[b]thiophenyl-1,1-dioxide)-homopiperazine;
(±) 1-(2-Benzo[b]thiophenyl-1,1-dioxide)-4-methyl-homopiperazine;
(±) 1-(2-Benzo[b]thiophenyl-1,1-dioxide)-4-ethyl-homopiperazine;
(±) 1-(2-Benzo[b]thiophenyl-1,1-dioxide)-4-benzyl-homopiperazine;
(±) 1-(2-Benzo[b]thiophenyl-1,1-dioxide)-1,4-diazacyclooctane;
(±) 1-(2-Benzo[b]thiophenyl-1,1-dioxide)-4-methyl-1,4-diazacyclooctane;
(±) 1-(2-Benzo[b]thiophenyl-1,1-dioxide)-4-ethyl-1,4-diazacyclooctane;
(±) 1-(2-Benzo[b]thiophenyl-1,1-dioxide)-4-benzyl-1,4-diazacyclooctane;
(±) 1-(2-Benzo[b]thiophenyl-1,1-dioxide)-1,5-diazacyclooctane;
(±) 1-(2-Benzo[b]thiophenyl-1,1-dioxide)-5-methyl-1,5-diazacyclooctane;
(±) 1-(2-Benzo[b]thiophenyl-1,1-dioxide)-5-ethyl-1,5-diazacyclooctane; or
(±) 1-(2-Benzo[b]thiophenyl-1,1-dioxide)-5-benzyl-1,5-diazacyclooctane;
or a pharmaceutically-acceptable addition salt thereof.

In another preferred embodiment, the chemical substance of the invention is a benzo[b]thiazole derivative of Formula IB, wherein X represents a group of Formula II, wherein n is 0, 1 or 2; m is 1, 2 or 3; and R represents hydrogen, alkyl, or aralkyl.

In a most preferred embodiment the benzo[b]thiazole derivative of the invention is
(±) 1-(2-Benzo[b]thiazolyl-1,1-dioxide)-imidazolidine;
(±) 1-(2-Benzo[b]thiazolyl-1,1-dioxide)-3-methyl-imidazolidine;
(±) 1-(2-Benzo[b]thiazolyl-1,1-dioxide)-1,3-diazacyclohexane;
(±) 1-(2-Benzo[b]thiazolyl-1,1-dioxide)-3-methyl-1,3-diazacyclohexane;
(±) 1-(2-Benzo[b]thiazolyl-1,1-dioxide)-piperazine;
(±) 1-(2-Benzo[b]thiazolyl-1,1-dioxide)-4-methyl-piperazine;
(±) 1-(2-Benzo[b]thiazolyl-1,1-dioxide)-4-ethyl-piperazine;
(±) 1-(2-Benzo[b]thiazolyl-1,1-dioxide)-4-benzyl-piperazine;
(±) 1-(2-Benzo[b]thiazolyl-1,1-dioxide)-homopiperazine;
(±) 1-(2-Benzo[b]thiazolyl-1,1-dioxide)-4-methyl-homopiperazine;
(±) 1-(2-Benzo[b]thiazolyl-1,1-dioxide)-4-ethyl-homopiperazine;

(±) 1-(2-Benzo[b]thiazolyl-1,1-dioxide)-4-benzyl-homopiperazine;
(±) 1-(2-Benzo[b]thiazolyl-1,1-dioxide)-1,4-diazacyclooctane;
(±) 1-(2-Benzo[b]thiazolyl-1,1-dioxide)-4-methyl-1,4-diazacyclooctane;
(±) 1-(2-Benzo[b]thiazolyl-1,1-dioxide)-4-ethyl-1,4-diazacyclooctane;
(±) 1-(2-Benzo[b]thiazolyl-1,1-dioxide)-4-benzyl-1,4-diazacyclooctane;
(±) 1-(2-Benzo[b]thiazolyl-1,1-dioxide)-1,5-diazacyclooctane;
(±) 1-(2-Benzo[b]thiazolyl-1,1-dioxide)-5-methyl-1,5-diazacyclooctane;
(±) 1-(2-Benzo[b]thiazolyl-1,1-dioxide)-5-ethyl-1,5-diazacyclooctane; or
(±) 1-(2-Benzo[b]thiazolyl-1,1-dioxide)-5-benzyl-1,5-diazacyclooctane;
or a pharmaceutically-acceptable addition salt thereof.

In a third preferred embodiment, the chemical substance of the invention is a benzo[b]thiophene derivative of Formula IA, wherein X represents a group of Formula III, wherein = represents a double bond; n is 0 or 1; and R represents hydrogen, alkyl or aralkyl.

In a most preferred embodiment the benzo[b]thiophene derivative of Formula IA is
(±) 3-(2-Benzo[b]thiophenyl-1,1-dioxide)-8-H-8-azabicyclo[3.2.1]oct-2-ene;
(±) 3-(2-Benzo[b]thiophenyl-1,1-dioxide)-8-methyl-8-azabicyclo[3.2.1]oct-2-ene;
(±) 3-(2-Benzo[b]thiophenyl-1,1-dioxide)-8-ethyl-8-azabicyclo[3.2.1]oct-2-ene;
(±) 3-(2-Benzo[b]thiophenyl-1,1-dioxide)-8-allyl-8-azabicyclo[3.2.1]oct-2-ene;
(±) 3-(2-Benzo[b]thiophenyl-1,1-dioxide)-8-benzyl-8-azabicyclo[3.2.1]oct-2-ene;
(±) 3-(2-Benzo[b]thiophenyl-1,1-dioxide)-9-H-9-azabicyclo[3.3.1]non-2-ene;
(±) 3-(2-Benzo[b]thiophenyl-1,1-dioxide)-9-methyl-9-azabicyclo[3.3.1]non-2-ene;
(±) 3-(2-Benzo[b]thiophenyl-1,1-dioxide)-9-ethyl-9-azabicyclo[3.3.1 ]non-2-ene;
(±) 3-(2-Benzo[b]thiophenyl-1,1-dioxide)-9-benzyl-9-azabicyclo[3.3.1]non-2-ene;
or a pharmaceutically-acceptable addition salt thereof.

In a fourth preferred embodiment, the chemical substance of the invention is a benzo[b]thiazole derivative of Formula IB, wherein X represents a group of Formula III, wherein = represents a double bond; n is 0 or 1; and R represents hydrogen, alkyl or aralkyl.

In a most preferred embodiment the benzo[b]thiazole derivative of Formula IB is
(±) 3-(2-Benzo[b]thiazolyl-1,1-dioxide)-8-H-8-azabicyclo[3.2.1]oct-2-ene;
(±) 3-(2-Benzo[b]thiazolyl-1,1-dioxide)-8-methyl-8-azabicyclo[3.2.1]oct-2-ene;
(±) 3-(2-Benzo[b]thiazolyl-1,1-dioxide)-8-ethyl-8-azabicyclo[3.2.1]oct-2-ene;
(±) 3-(2-Benzo[b]thiazolyl-1,1-dioxide)-8-benzyl-8-azabicyclo[3.2.1]oct-2ene;
(±) 3-(2-Benzo[b]thiazolyl-1,1-dioxide)-9-H-9-azabicyclo[3.3.1]non-2-ene;
(±) 3-(2-Benzo[b]thiazolyl-1,1-dioxide)-9-methyl-9-azabicyclo[3.3.1]non-2-ene;
(±) 3-(2-Benzo[b]thiazolyl-1,1-dioxide)-9-ethyl-9-azabicyclo[3.3.1]non-2-ene; or
(±) 3-(2-Benzo[b]thiazolyl-1,1-dioxide)-9-benzyl-9-azabicyclo[3.3.1]non-2-ene;
or a pharmaceutically-acceptable addition salt thereof.

In a fifth preferred embodiment, the chemical substance of the invention is a benzo[b]thiophene derivative of Formula IA, wherein X represents a group of Formula IV, wherein = represents a double bond; n is 0 or 1, and R represents hydrogen or alkyl.

In a most preferred embodiment the benzo[b]thiophene derivative of Formula IA is
(±) 3-(2-Benzo[b]thiophenyl-1,1-dioxide)-7-H-7-azabicyclo[3.3.0]oct-2-ene;
(±) 3-(2-Benzo[b]thiophenyl-1,1-dioxide)-7-methyl-7-azabicyclo[3.3.0]oct-2-ene;
(±) 3-(2-Benzo[b]thiophenyl-1,1-dioxide)-7-ethyl-7-azabicyclo[3.3.0]oct-2-ene; or
(±) 3-(2-Benzo[b]thiophenyl-1,1-dioxide)-7-benzyl-7-azabicyclo[3.3.0]oct-2-ene;
or a pharmaceutically-acceptable addition salt thereof.

In a sixth preferred embodiment, the chemical substance of the invention is a benzo[b]thiazole derivative of Formula IB, wherein X represents a group of Formula IV, wherein = represents a double bond; n is 0 or 1; and R represents hydrogen or alkyl.

In a most preferred embodiment the benzo[b]thiazole derivative of Formula IB is
(±) 3-(2-Benzo[b]thiazolyl-1,1-dioxide)-7-H-7-azabicyclo[3.3.0]oct-2-ene;
(±) 3-(2-Benzo[b]thiazolyl-1,1-dioxide)-7-methyl-7-azabicyclo[3.3.0]oct-2-ene;
(±) 3-(2-Benzo[b]thiazolyl-1,1-dioxide)-7-ethyl-7-azabicyclo[3.3.0]oct-2-ene; or
(±) 3-(2-Benzo[b]thiazolyl-1,1-dioxide)-7-benzyl-7-azabicyclo[3.3.0]oct-2-ene;
or a pharmaceutically-acceptable addition salt thereof.

In a seventh preferred embodiment, the chemical substance of the invention is a benzo[b]thiophene derivative of Formula IA, wherein X represents a group of Formula V, wherein n is 0, 1 or 2; m is 1 or 2; and R represents hydrogen or alkyl.

In a most preferred embodiment the benzo[b]thiophene derivative of Formula IA is
(±) 3-(2-Benzo[b]thiophenyl-1,1-dioxide)-9-H-3,9-diazabicyclo-[4.2.1]-nonane;
(±) 3-(2-Benzo[b]thiophenyl-1,1-dioxide)-9-methyl-3,9-diazabicyclo[4.2.1]-nonane;
(±) 3-(2-Benzo[b]thiophenyl-1,1-dioxide)-9-ethyl-3,9-diazabicyclo-[4.2.1]-nonane;
(±) 3-(2-Benzo[b]thiophenyl-1,1-dioxide)-10-H-3,10-diazabicyclo-[4.3.1]-decane;
(±) 3-(2-Benzo[b]thiophenyl-1,1-dioxide)-10-methyl-3,10-diazabicyclo-[4.3.1]-decane;
(±) 3-(2-Benzo[b]thiophenyl-1,1-dioxide)-10-ethyl-3,10-diazabicyclo-[4.3.1]-decane;
or a pharmaceutically-acceptable addition salt thereof.

In an eight preferred embodiment, the chemical substance of the invention is a benzo[b]thiazole derivative of Formula IB, wherein X represents a group of Formula V, wherein n is 0, 1 or 2; m is 1 or 2; and R represents hydrogen or alkyl.

In a most preferred embodiment the benzo[b]thiazole derivative of Formula IB is
(±) 3-(2-Benzo[b]thiazolyl-1,1-dioxide)-9-H-3,9-diazabicyclo-[4.2.1]-nonane;
(±) 3-(2-Benzo[b]thiazolyl-1,1-dioxide)-9-methyl-3,9-diazabicyclo-[4.2.1]-nonane;
(±) 3-(2-Benzo[b]thiazolyl-1,1-dioxide)-9-ethyl-3,9-diazabicyclo-[4.2.1]-nonane;

(±) 3-(2-Benzo[b]thiazolyl-1,1-dioxide)-10-H-3,10-diazabicyclo-[4.3.1]-decane;

(±) 3-(2-Benzo[b]thiazolyl-1,1-dioxide)-10-methyl-3,10-diazabicyclo-[4.3.1]-decane; or (±) 3-(2-Benzo[b]thiazolyl-1,1-dioxide)-10-ethyl-3,10-diazabicyclo-[4.3.1]-decane;

or a pharmaceutically-acceptable addition salt thereof.

In a ninth preferred embodiment, the chemical substance of the invention is a benzo[b]thiophene derivative of Formula IA, wherein X represents a group of Formula VI, wherein n is 0 or 1; and R represents hydrogen, alkyl, phenyl or benzyl.

In a most preferred embodiment the benzo[b]thiophene derivative of Formula IA is (±) 3-(2-Benzo[b]thiophenyl-1,1-dioxide)-7-H-3,7-diazabicyclo[3.3.0]octane;

(±) 3-(2-Benzo[b]thiophenyl-1,1-dioxide)-7-methyl-3,7-diazabicyclo[3.3.0]octane;

(±) 3-(2-Benzo[b]thiophenyl-1,1-dioxide)-7-phenyl-3,7-diazabicyclo[3.3.0]octane;

(±) 3-(2-Benzo[b]thiophenyl-1,1-dioxide)-7-benzyl-3,7-diazabicyclo[3.3.0]octane;

(±) 3-(2-Benzo[b]thiophenyl-1,1-dioxide)-7-H-3,7-diazabicyclo[3.3.1]nonane;

(±) 3-(2-Benzo[b]thiophenyl-1,1-dioxide)-7-methyl-3,7-diazabicyclo[3.3.1]nonane;

(±) 3-(2-Benzo[b]thiophenyl-1,1-dioxide)-7-phenyl-3,7-diazabicyclo[3.3.1]nonane;

(±) 3-(2-Benzo[b]thiophenyl-1,1-dioxide)-7-benzyl-3,7-diazabicyclo[3.3.1]nonane;

or a pharmaceutically-acceptable addition salt thereof.

In a tenth preferred embodiment, the chemical substance of the invention is a benzo[b]thiazole derivative of Formula IB, wherein X represents a group of Formula VI, wherein n is 0 or 1; and R represents hydrogen, alkyl, phenyl or benzyl.

In a most preferred embodiment the benzo[b]thiazole derivative of Formula IB is (±) 3-(2-Benzo[b]thiazolyl-1,1-dioxide)-7-H-3,7-diazabicyclo[3.3.0]octane;

(±) 3-(2-Benzo[b]thiazolyl-1,1-dioxide)-7-methyl-3,7-diazabicyclo[3.3.0]octane;

(±) 3-(2-Benzo[b]thiazolyl-1,1-dioxide)-7-phenyl-3,7-diazabicyclo[3.3.0]octane;

(±) 3-(2-Benzo[b]thiazolyl-1,1-dioxide)-7-benzyl-3,7-diazabicyclo[3.3.0]octane;

(±) 3-(2-Benzo[b]thiazolyl-1,1-dioxide)-7-H-3,7-diazabicyclo[3.3.1]nonane;

(±) 3-(2-Benzo[b]thiazolyl-1,1-dioxide)-7-methyl-3,7-diazabicyclo[3.3.1]nonane;

(±) 3-(2-Benzo[b]thiazolyl-1,1-dioxide)-7-phenyl-3,7-diazabicyclo[3.3.1]nonane; or (±) 3-(2-Benzo[b]thiazolyl-1,1-dioxide)-7-benzyl-3,7-diazabicyclo[3.3.1]nonane;

or a pharmaceutically-acceptable addition salt thereof.

In an eleventh preferred embodiment, the chemical substance of the invention is a benzo[b]thiophene derivative of Formula IA, wherein X represents a group of Formula VII, wherein R represents hydrogen or alkyl.

In a most preferred embodiment the benzo[b]thiophene derivative of Formula IA is (±) 2-(2-Benzo[b]thiophenyl-1,1-dioxide)-(1S,4S)-(+)-5-H-2,5-diazabicyclo-[2.2.1]-heptane;

(±) 2-(2-Benzo[b]thiophenyl-1,1-dioxide)-(1S,4S)-(+)-5-methyl-2,5-diazabicyclo-[2.2.1]-heptane;

or a pharmaceutically-acceptable addition salt thereof.

In a twelve preferred embodiment, the chemical substance of the invention is a benzo[b]thiazole derivative of Formula IB, wherein X represents a group of Formula VII, wherein R represents hydrogen or alkyl.

In a most preferred embodiment the benzo[b]thiazole derivative of Formula IB is (±) 2-(2-Benzo[b]thiazolyl-1,1-dioxide)-(1S,4S)-(+)-5-H-2,5diazabicyclo-[2.2.1]-heptane; or (±) 2-(2-Benzo[b]thiazolyl-1,1-dioxide)-(1S,4S)-(+)-5-methyl-2,5-diazabicyclo-[2.2.1]-heptane;

or a pharmaceutically-acceptable addition salt thereof.

In a thirteenth preferred embodiment, the chemical substance of the invention is a benzo[b]thiophene derivative of Formula IA, wherein X represents a group of Formula VIII, wherein = represents a single bond or a double bond.

In a most preferred embodiment the benzo[b]thiophene derivative of Formula IA is (±) 3-(2-Benzo[b]thiophenyl-1,1-dioxide)-quinuclidine;

(±) 3-(2-Benzo[b]thiophenyl-1,1-dioxide)-quinuclidine-2-ene; or (±)-3-(2-Benzothiophenyl-1,1-dioxide)quinuclidine-2-ene-N-methyl;

or a pharmaceutically-acceptable addition salt thereof.

In a fourteenth preferred embodiment, the chemical substance of the invention is a benzo[b]thiazole derivative of Formula IB, wherein X represents a group of Formula VIII, wherein = represents a single bond or a double bond.

In a most preferred embodiment the benzo[b]thiazole derivative of Formula IB is (±) 3-(2-Benzo[b]thiazolyl-1,1-dioxide)-quinuclidine; or (±) 3-(2-Benzo[b]thiazolyl-1,1-dioxide)-quinuclidine-2-ene;

or a pharmaceutically-acceptable addition salt thereof.

Definition of Substituents

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention an alkenyl group designates a carbon chain containing one or more double bonds, including di-enes, tri-enes and poly-enes. In a preferred embodiment the alkenyl group of the invention comprises of from two to eight carbon atoms ($C_{2-8}$-alkenyl), more preferred of from two to six carbon atoms ($C_{2-6}$-alkenyl), including at least one double bond. In a most preferred embodiment the alkenyl group of the invention is ethenyl; 1- or 2-propenyl; 1-, 2- or 3-butenyl, or 1,3-butdienyl; 1-, 2-, 3-, 4 or 5-hexenyl, or 1,3-hexdienyl, or 1,3,5-hextrienyl; 1-, 2-, 3-, 4- , 5-, 6-, or 7-octenyl, or 1,3-octdienyl, or 1,3,5-octtrienyl, or 1,3,5,7-octtetraenyl.

In the context of this invention an alkynyl group designates a carbon chain containing one or more triple bonds, including di-ynes, triynes and poly-ynes. In a preferred embodiment the alkynyl group of the invention comprises of from two to eight carbon atoms ($C_{2-8}$alkynyl), more preferred of rom two to six carbon atoms ($C_{2-8}$-alkynyl), including at least one triple bond. In its most preferred embodiment the alkynyl group of the invention is ethynyl; 1-, or 2-propynyl; 1-, 2-, or 3-butynyl, or 1,3-butdiynyl; 1-, 2-, 3-, 4-pentynyl, or 1,3-pentdiynyl; 1-, 2-, 3-, 4-, or 5-henynyl, or 1,3-hexdiynyl or 1,3,5-hextriynyl; 1-, 2-, 3-, 4-, 5- or 6-heptynyl, or 1,3-heptdiynyl, or 1,3,5-heptriynyl; 1-, 2-, 3-, 4-, 5-, 6- or 7-octynyl, or 1,3-octdiynyl, or 1,3,5-octtriynyl, or 1,3,5,7-octtetraynyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an aryl group designates a monocyclic or polycyclic aromatic hydrocarbon group. Examples of preferred aryl groups of the invention include phenyl, indenyl, naphthyl, azulenyl, fluorenyl, and anthracenyl.

In the context of this invention an aralkyl group designates an aryl group as defined above, which aryl group is attached to an alkyl group as also defined above. Examples of preferred aralkyl groups of the invention include benzyl.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived rom lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Metal salts of a chemical compound of the invention include alkali metal salts such as the sodium salt of a chemical compound of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Steric Isomers

The chemical compounds of the present invention may exist in (+) and (−) forms as well as in racemic forms (±). The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l- (tartrates, mandelates, or camphorsulphonate) salts for example.

The chemical compounds of the present invention may also be resolved by the formation of diastereomeric amides by reaction of the chemical compounds of the present invention with an optically active-activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers. Racemates, and Resolutions*", John Wiley and Sons, New York (1981).

Optical active compounds can also be prepared from optical active starting materials.

Methods of Preparation

The chemical substances of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The present invention relates to novel chemical substances, which are found to be cholinergic ligands at the nicotinic acetylcholine receptors (nAChR), and modulators of the monoamine receptors, in particular the biogenic amine transporters 5-HT, DA and NE. Also preferred compounds of the invention show selective α7 activity.

In the context of this invention the term "modulator" covers agonists, partial agonists, antagonists and allosteric modulators of the receptor.

Due to their pharmacological profile the compounds of the invention may 25 be useful for the treatment of diseases or conditions as diverse as CNS related diseases, PNS related diseases, diseases related to smooth muscle contraction, endocrine disorders, diseases related to neuro-degeneration, diseases related to inflammation, pain, and withdrawal symptoms caused by the termination of abuse of chemical substances.

In a preferred embodiment the compounds of the invention are used for the treatment of diseases, disorders, or conditions relating to the central nervous system. Such diseases or disorders includes anxiety, cognitive disorders, learning deficit, memory deficits and dysfunction, Alzheimer's disease, attention deficit, attention deficit hyperactivity disorder, Parkinson's disease, Huntington's disease, Amyotrophic Lateral Sclerosis, Gilles de la Tourette's syndrome, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatc syndrome, social phobia, sleeping disorders, pseudodementia, Ganser's syndrome, pre-menstrual syndrome, late luteal phase syndrome, chronic fatigue syndrome, mutism, trichotillomania, and jet-lag.

In another preferred embodiment the compounds of the invention may be useful for the treatment of diseases, disorders, or conditions associated with smooth muscle contractions, including convulsive disorders, angina pectoris, premature labour, convulsions, diarrhoea, asthma, epilepsy, tardive dyskinesia, hyperkinesia, premature ejaculation, and erectile difficulty.

In yet another preferred embodiment the compounds of the invention may be useful for the treatment of endocrine disorders, such as thyrotoxicosis, pheochromocytoma, hypertension and arrhythmias.

In still another preferred embodiment the compounds of the invention may be useful for the treatment of neurodegenerative disorders, including transient anoxia and induced neuro-degeneration.

In even another preferred embodiment the compounds of the invention may be useful for the treatment of inflammatory diseases, disorders, or conditions, including inflammatory skin disorders such as acne and rosacea, Chron's disease, inflammatory bowel disease, ulcerative colitis, and diarrhoea.

In still another preferred embodiment the compounds of the invention may be useful for the treatment of mild, moderate or even severe pain of acute, chronic or recurrent character, as well as pain caused by migraine, postoperative pain, and phantom limb pain.

Finally the compounds of the invention may be useful for the treatment of withdrawal symptoms caused by termination of use of addictive substances. Such addictive substances include nicotine containing products such as tobacco, opioids such as heroin, cocaine and morphine, benzodiazepines and benzodiazepine-like drugs, and alcohol. Withdrawal from addictive substances is in general a traumatic experience characterised by anxiety and frustration, anger, anxiety, difficulties in concentrating, restlessness, decreased heart rate and increased appetite and weight gain.

In this context "treatment" covers treatment, prevention, prophylactics and alleviation of withdrawal symptoms and abstinence as well as treatment resulting in a voluntary diminished intake of the addictive substance.

In another aspect, the compounds of the invention are used as diagnostic agents, e.g. for the identification and localisation of nicotinic receptors in various tissues.

Neuroimaging

The chemical substances of the invention may be useful as diagnostic tools or monitoring agents in various diagnostic methods, and in particular for in vivo receptor imaging (neuroimaging).

In another aspect of the invention, a method for the non-invasive determination of the distribution of a tracer compound inside a whole, intact living animal or human body using a physical detection method is provided. According to this method a tracer compound is a compound of the invention, or any of its enantiomers or any mixture thereof, an N oxide thereof, a pharmaceutically acceptable salt thereof, in a labelled or un-labelled form.

In a preferred embodiment the physical detection method is selected from PET, SPECT; MRS, MRI, CAT, or combinations thereof.

The labelled compound of the invention preferably contains at least one radionuclide asa label. Positron emitting radionuclides are all candidates for usage. In the context of this invention the radionuclide is preferably selected from $^{2}H$ (deuterium), $^{3}H$ (tritium), $^{11}C$, $^{13}C$, $^{14}C$, $^{15}O$, $^{13}N$, $^{123}I$, $^{125}I$, $^{131}I$, $^{18}F$ and $^{99m}Tc$.

An example of commercially available labelling agents, which can be used in the preparation of the labelled compounds of the present invention is $[^{11}C]O_2$, $^{18}F$, and NaI with different isotopes of Iodine.

In particular $[^{11}C]O_2$ may be converted to a $[^{11}C]$-methylating agent, such as $[^{11}C]H_3l$ or $[^{11}C]$-methyl triflate.

The tracer compound can be selected in accordance with the detection method chosen.

In one preferred embodiment, the labelled or unlabelled compound of the invention can be detected by a suitable spectroscopic method, in particular UV spectroscopy and/or fluorescence spectroscopy.

In anther preferred embodiment, the compounds of the invention labelled by incorporation of a isotope into the molecule, which may in particular be an isotope of the naturally occurring atoms including $^{2}H$ (deuterium), $^{3}H$ (tritium), $^{11}C$, $^{13}C$, $^{14}C$, $^{15}O$, $^{13}N$, $^{123}I$, $^{125}I$, $^{131}I$, $^{18}F$ and $^{99m}Tc$, and the isotope incorporation may be measured by conventional scintillation counting techniques.

In a third preferred embodiment, the physical method for detecting said tracer compound of the present invention is selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Before conducting the method of the present invention, a diagnostically effective amount of a labelled or unlabelled compound of the invention is administered to a living body, including a human.

The compounds of the invention is believed to be particularly suited for in vivo receptor imaging (neuroimaging).

In a particularly preferred embodiment the physical method for detecting the compound of the invention is Position Emission Tomography (PET).

It is currently believed that the diagnostically effective amount of the labelled or unlabelled compound of the invention, to be administered before conducting the in vivo method for the invention, is within a range of from 0.1 ng to 100 mg per kg body weight, preferably within a range of from 1 ng to 10 mg per kg body weight.

Pharmaceutical Compositions

In another aspect the invention provides novel pharmaceutical compositions comprising a therapeutically effective amount of the chemical substance of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical substance of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by any skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

The chemical substances of the present invention are valuable nicotinic and monoamine receptor modulators, and therefore useful for the treatment of a range of ailments involving cholinergic dysfunction as well as a range of disorders responsive to the action of nAChR modulators.

In another aspect the invention provides a method for the treatment, prevention or alleviation of a disease or a disorder or a condition of a living animal body, including a human, which disease, disorder or condition is responsive to modulation of cholinergic receptors and/or monoamine receptors, and which method comprises administering to such a living animal body, including a human, in need thereof an effective amount of a compound of the invention.

In a preferred embodiment, the disease, disorder or condition relates to the central nervous system.

In a preferred embodiment, the disease, disorder or condition is anxiety, cognitive disorders, learning deficit, memory deficits and dysfunction, Alzheimer's disease, attention deficit, attention deficit hyperactivity disorder, Parkinson's disease, Huntington's disease,. Amyotrophic Lateral Sclerosis, Gilles de la Tourette's syndrome, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, sleeping disorders, pseudodementia, Ganser's syndrome, premenstrual syndrome, late luteal phase syndrome, chronic fatigue syndrome, mutism, trichotillomania, and jet-lag.

In a another preferred embodiment, the disease, disorder or condition are associated with smooth muscle contractions, including convulsive disorders, angina pectoris, premature labour, convulsions, diarrhoea, asthma, epilepsy, tardive dyskinesia, hyperkinesia, premature ejaculation, and erectile difficulty.

In a third preferred embodiment, the disease, disorder or condition is related to the endocrine system, such as thyrotoxicosis, pheochromocytoma, hypertension and arrhythmias.

In a fourth preferred embodiment, the disease, disorder or condition is a neurodegenerative disorders, including transient anoxia and induced neuro-degeneration.

In a fifth preferred embodiment, the disease, disorder or condition is an inflammatory disorder, including inflammatory skin disorders such as acne and rosacea, Chron's disease, inflammatory bowel disease, ulcerative colitis, and diarrhoea.

In a sixth preferred embodiment, the disease, disorder or condition is mild, moderate or even severe pain of acute, chronic or recurrent character, as well as pain caused by migraine, postoperative pain, and phantom limb pain.

In a seventh preferred embodiment, the disease, disorder or condition is associated with withdrawal symptoms caused by termination of use of addictive substances, including nicotine containing products such as tobacco, opioids such as heroin, cocaine and morphine, benzodiazepines and benzodiazepine-like drugs, and alcohol.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Preferred ranges are from about 0.001 to about 1 mg/kg i.v. and from about 0.1 to about 10 mg/kg p.o.

EXAMPLES

The invention is further illustrated with reference to the following examples, which are not intended to be in any way limiting to the scope of the invention as claimed.

Example 1

Preparatory Example

All reactions involving air sensitive reagents or intermediates were performed under nitrogen and in anhydrous solvents. Magnesium sulfate was used as drying agent in the workup-procedures and solvents were evaporated under reduced pressure.

(±)-3-(2-Benzo[b]thiophenyl)-8-methyl-8-azabicyclo[3.2.1]oct-2-ene hydrochloric acid salt To a mixture of benzo[b]thiophene (20.2 g, 151 mmol) and diethyl ether (200 ml), butyllithium in hexane (2.5 M, 66 ml, 166 mmol) was added at room temperature. The mixture was stirred at reflux temperature for 1 hour and then cooled to −70° C. Tropinone (21.4 g, 154 mmol) solved in diethyl ether (150 ml) was added at −70° C. and stirred for 1 hour. The reaction mixture was allowed to warm to room temperature overnight. Aqueous sodium hydroxide (200 ml, 1 M) was added, and endo and exo-3-(2-benzo[b]thiophenyl)-3-hydroxy-8-methyl-8-azabicyclo[3.2.1]octane was isolated by filtration. Yield 46.8 g, 96%.

A mixture of endo and exo-3-(2-benzofuryl)-3-hydroxy-8-methyl-8-azabicyclo[3.2.1]octane (46.8 g, 116.6 mmol), hydrochloric acid (500 ml, 25%) was stirred at reflux for 5 hours. The solvent was evaporated. Yield 100%. Mp 298° C.

(±)-3-(2-Benzo[b]thiophenyl)-8-H-8-azabicyclo[3.2.1]oct-2-ene hydrochloric acid salt A mixture of (±)-3-(2-benzothienyl)-8-methyl-8-azabicyclo[3.2.1]oct-2-ene hydrochloric acid (24.4 g, 0.0955 mol), 1-chloroethyl-chloroformate (15.5 ml, 0.143 mol) and xylene (200 ml) was heated and stirred at reflux temperature for 24 hours. Methanol (300 ml) was added followed by stirring and heating at reflux temperature for 22 hours. The mixture was cooled to room-temperature and the product was filtered. The crude product was recrystallised from diethyl ether. Yield 16 g (69%). Mp 252-259° C.

(±)-3-(2-Benzo[b]thiophenyl)-8-tert-butoxycarbonyl-8-azabicyclo[3.2.1]oct-2-ene A mixture of (±)-3-(2-benzo[b]thiophenyl)-8-H-butoxycarbonyl-8-azabicyclo[3.2.1]oct-2-ene (7.72 g, 32 mmol), triethylamine (4.5 ml, 32 mmol), di-tert-butyl dicarbonate (7.0 g, 32 mmol) and dichloromethane (50 ml) was stirred for 2 hours. The mixture was washed with aqueous sodium hydroxide (50 ml, 1 M). Yield 9.38 g, 86%.

(±)-3-(2-Benzo[b]thiophenyl-1,1-dioxide)-8-tert-butoxycarbonyl-8-azabicyclo[3.2.1]oct-2-ene A mixture of (±)-3-(2-benzo[b]thiophenyl)-8-tert-butoxycarbonyl-8-azabicyclo[3.2.1]oct-2-ene (4.5 g, 13.2 mmol), m-chlormperbenzoic acid (10.0 g, 58 mmol) and chloroform (50 ml) was stirred at room temperature for 4 hours. The mixture was filtered and the filtrate was evaporated. Aqueous sodium hydroxide (100 ml, 1 M) was added and the mixture was extracted with diethyl ether (3×50 ml). The crude material was purified by chromatography, using a mixture (1:3) of EtAc and heptane. The title compound was isolated. Yield 3.31 g, 67%.

(±)-3-(2-Benzo[b]thiophenyl-1,1-dioxide)-8-H-8-azabicyclo[3.2.1]oct-2-ene fumaric acid salt (Compound 1)

A mixture of (±)3-(2-benzo[b]thiophenyl-1,1-dioxide)-8-tert-butoxycarbonyl-8-azabicyclo[3.2.1]oct-2-ene (2.95 g, 7.9 mmol), trifluoroacetic acid (5.9 ml, 79 mmol) and dichloromethane (50 ml). The mixture was evaporated. Aqueous sodium hydroxide (30 ml, 1 M) was added followed by extraction with ethyl acetate (3×30 ml). Chromatography on silica gel with dichloromethane, methanol and conc. ammonia (89:10:1) gave the title compound. Yield 1.52 g, 70%. The corresponding salt was obtained by addition of a diethyl ether and methanol mixture (9:1) saturated with fumaric acid. Mp 261-265° C.

(±)-3-2-Benzo[b]thiophenyl-1,1-dioxide)-8-methyl-8-azabicyclo[3.2.1]oct-2-ene fumaric acid salt (Compound 2)

A mixture of (±)3-(2-benzo[b]thiophenyl-1,1-dioxide)-8-H-8-azabicyclo[3.2.1]oct-2-ene (0.56 g, 2.05 mmol), formic acid (2.3 ml, 61.5 mmol) and formaldehyde (1.7 ml, 61.5 mmol) was stirred at 100° C. over night. The mixture was evaporated. Aqueous sodium hydroxide (30 ml, 1 M) was added followed by extraction with ethyl acetate (3×30 ml). Chromatography on silica gel with dichloromethane, methanol and conc. ammonia (89:10:1) gave the title compound. The corresponding salt was obtained by addition of a diethyl ether and methanol mixture (9:1) saturated with fumaric acid. Yield 0.42 g, 51%. Mp 198.6-203.4° C.

(±)-3-(2-Benzo[b]thiophenyl-1,1-dioxide)-8-allyl-8-azabicyclo[3.2.1]oct-2-ene (Compound 3)

A mixture of (±)3-(2-benzo[b]thiophenyl-1,1-dioxide)-8-H-8-azabicyclo[3.2.1]oct-2-ene (0.16 g, 0.58 mmol), 3-bromo-1-propene (54 ul, 0.64 mmol), diisopropylethylamine (102 ul, 0.58 mmol), DMF (10 ml) was stirred at 80° C. for 2 days. Aqueous sodium hydroxide (20 ml, 1 M) was added. The mixture was extracted with diethylether (3×30 ml). Chromatography on silica gel with dichloromethane, methanol and conc. ammonia (89:10:1) gave the title compound as an oil. Yield: 50 mg (28%).

(±)-3-(2-Benzo[b]thiophenyl-1,1-dioxide)-8-ethyl-8-azabicyclo[3.2.1]oct-2-ene (Compound 4)

A mixture of (±)3-(2-benzo[b]thiophenyl-1,1-dioxide)-8-H-8-azabicyclo[3.2.1]oct-2-ene (0.18 g, 0.66 mmol), 3-bromoethane (54 ul, 0.72 mmol), diisopropylethylamine (115 ul, 0.66 mmol), DMF (10 ml) was stirred at 80° C. for 2 days. Aqueous sodium hydroxide (20 ml, 1 M) was added. The mixture was extracted with diethylether (3×30 ml). Chromatography on silica gel with dichloromethane, methanol and conc. ammonia (89:10:1) gave the title compound as an oil. Yield: 30 mg (15%).

(±)-3-(2-Benzothiophenyl)-quinuclidine-2-ene (Intermediate compound)

To a mixture of benzothiophene (20.5 g, 154 mmol) in diethyl ether at 20° C. was added: butyllithium (67 ml, 2.5 M). The mixture was stirred at room temperature for 30 minutes. 3-Quinuclidinone (19.2 g, 153 mmol) solved in diethylether (200 ml) was added to the mixture at −70° C. followed by stirring at the same temperature for 1 hour. The temperature was allowed to reach room temperature. Water (10 ml) was added, followed by aqueous sodium hydroxide (200 ml, 1 M). The mixture was stirred, filtered and washed with diethyl ether (50 ml). Yield (of the alcohol): 33.55 g (84%). A mixture of the alcohol (10.0 g, 38.6 mmol) and hydrochloric acid (100 ml, 25%) was stirred at 70° C. for 3 days. The mixture was evaporated. Aqueous sodium hydroxide (125 ml, 1 M) was added, and the mixture was extracted with diethyl ether.

Chromatography on silica gel with dichloromethane, methanol and conc. ammonia (89:10:1) gave the title compound. Yield: 8.33 g (88%).

(±)-3-(2-Benzothiophenyl-1,1-dioxide)-quinuclidine-2-ene-N-oxide (Intermediate compound)

A mixture of (±)-3-(2-benzothiophenyl)quinuclidine-2-ene (3.0 g, 12.3 mmol) m-chloroperbenzoic acid (12.76 g, 74 mmol) and 50 ml dichloromethane was stirred for 15 hours. The mixture was filtered, the solid was washed with dichloromethane and the filtrate was purified by chromatography on silica gel with dichloromethane, methanol and conc. ammonia (89:10:1) gave the title compound as a solid. Mp 125-135° C.

(±)-3-(2-Benzothiophenyl-1,1-dioxide)-quinuclidine-2-ene fumaric acid salt (Compound 5)

A mixture of (±)-3-(2-benzothiophenyl-1,1-dioxide)-quinuclidine-2-ene-N-oxide (1.35 g, 4.7 mmol), triphenylphosphine (3.67 g, 14.0 mmol) and dioxane (30 ml) was stirred at reflux for 2 hours. The solvent was evaporated, aqueous sodium hydroxide (100 ml, 1 M) was added and the mixture was extracted with dichloromethane (2×50 ml). Chromatography on silica gel with dichloromethane, methanol and conc. ammonia (89:10:1) gave the title compound as free base. The corresponding salt was obtained by addition of a diethyl ether and methanol mixture (9:1) saturated with fumaric acid. Mp 233° C.

(±)-3-2-Benzothiophenyl-1,1-dioxide)-quinuclidine-2-ene-N-methyl iodide salt (Compound 6)

A mixture of (±)-3-(2-Benzothiophenyl-1,1-dioxide)-quinuclidine-2-ene (100 mg, 0.4 mmol), methyl iodide (75 mg, 0.5 mmol) and 5 ml dichloromethane was stirred at room temperature for 15 hours. The mixture was evaporated. The solid was triturated with diethylether (10 ml). Yield 100 mg (95%). Mp 226.3° C.

Example 2

In Vitro Inhibition of $^3$H-α-Bungarotoxine Binding in Rat Brain

In this example, the affinity of the compounds of the invention for binding to $α_7$-subtype of nicotinic receptors is determined.

α-Bungarotoxine is a peptide isolated from the venom of the Elapidae snake *Bungarus multicinctus*. It has high affinity for neuronal and neuromuscular nicotinic receptors, where it acts as a potent antagonist.

$^3$H-α-Bungarotoxine labels nicotinic acetylcholine receptors formed by the $α_7$ subunit isoform found in brain and the $α_1$ isoform in the neuromuscular junction.

Tissue Preparation

Preparations are performed at 0-4° C. Cerebral cortices from male Wistar rats (150-250 g) are homogenised for 10 seconds in 15 ml of 20 mM Hepes buffer containing 118 mM NaCl, 4.8 mM KCl, 1.2 mM $MgSO_4$ and 2.5 mM $CaCl_2$ (pH 7.5) using an Ultra-Turrax homogeniser. The tissue suspension is subjected to centrifugation at 27,000×g for 10 minutes. The supernatant is discarded and the pellet is washed twice by centrifugation at 27,000×g for 10 minutes in 20 ml of fresh buffer, and the final pellet is then re-suspended in fresh buffer containing 0.01% BSA (35 ml per g of original tissue) and used for-binding assays.

Assay

Aliquots of 500 μl of homogenate are added to 25 μl of test solution and 25 μl of $^3$H-α-bungarotoxine (2 nM, final concentration) and mixed and incubated for 2 hours at 37° C. Non-specific binding is determined using (−)-nicotine (1 mM, final concentration). After incubation, the samples are added 5 ml of ice-cold Hepes buffer containing 0.05% PEI and poured directly onto Whatman GF/C glass fibre filters (pre-soaked in 0.1% PEI for at least 6 hours) under suction, and immediately washed with 2×5 ml ice-cold buffer.

The amount of radioactivity on the filters is determined by conventional liquid scintillation counting. Specific binding is total binding minus non-specific binding.

The test value is given as an $IC_{50}$ (the concentration of the test substance which inhibits the specific binding of $^3$H-α-bungarotoxin by 50%).

The results of these experiments are presented in Table 1 below.

TABLE 1

| Inhibition of $^3$H-α-Bungarotoxine Binding | |
|---|---|
| Compound No. | $IC_{50}$ (μM) |
| Compound 2 | 0.018 |
| Compound 3 | 0.85 |

Example 3

In Vitro Inhibition of $^3$H-5-Hydroxytyptamine Uptake in Cortical Synaptosomes

Serotonin transporters/uptake sites on nerve terminals presumably function to terminate neuronal signaling by removing serotonin from the synaptic cleft. The activity of the serotonin transporter integral protein can be measured in vitro by synaptosomal uptake of $^3$H-5-hydroxytryptamine (5-HT, serotonin).

Preparations are performed at 0-4° C. Cerebral cortices from male Wistar rats (150-200 g) are homogenized for 5-10 seconds in 100 volumes of ice-cold 0.32 M sucrose containing 1 mM pargyline, using a motor driven teflon pestle in a glass homogenizing vessel. Monoamine oxidase activity is inhibited in the presence of pargyline.

The homogenate is subjected to centrifugation at 1000×g for 10 minutes. The resulting supernatant is then centrifuged at 27,000×g for 50 minutes and the supernatant is discarded. The pellet ($P_2$) is resuspended in oxygenated (equilibrated with an atmosphere of 96% $O_2$: 4% $CO_2$ for at least 30 minutes) Krebs-Ringer incubation buffer (1000 ml per g of original tissue) at pH 7.2 containing 122 mM NaCl, 0.16 mM EDTA, 4.8 mM KCl, 12.7 mM $Na_2HPO_4$, 3.0 mM $NaH_2PO_4$, 1.2 mM $MgSO_4$, 1 mM $CaCl_2$, 10 mM glucose and 1 mM ascorbic acid.

Aliquots of 4.0 ml tissue suspension are added to 100 μl of test solution and 100 μl of ³H-5-HT (1 nM, final concentration), mixed and incubated for 30 minutes at 37° C. Non-specific uptake is determined using Citalopram (1 μM, final concentration, available from Lundbeck, Denmark).

After incubation, the samples are poured directly onto Whatman GF/C glass fibre filters under suction. The filters are washed three times with 5 ml of ice-cold 0.9% (w/v) NaCl solution.

The amount of radioactivity on the filters is determined by conventional liquid scintillation counting. Specific uptake is calculated as the difference between total uptake and non-specific uptake.

25-75% inhibition of specific binding must be obtained, before calculation of an $IC_{50}$.

The test value is given as $IC_{50}$ (the concentration (μM) of the test substance which inhibits the specific binding of ³H-5-HT by 50%).

The results are presented in Table 2 below.

TABLE 2

Inhibition of ³H-5-Hydroxytryptamine Uptake

| Compound No. | $IC_{50}$ (μM) |
|---|---|
| Compound 1 | 0.19 |
| Compound 2 | 0.66 |

The invention claimed is:

1. A chemical substance represented by Formula I

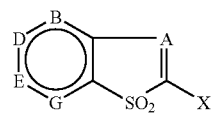

(I)

any of its enantiomers or any mixture of enantiomers, or a pharmaceutically-acceptable addition salt thereof, wherein A, B, D, E and G, independently of each another, represent a carbon (C) or a nitrogen (N) atom, constituting an aromatic ring system; and X represents a group of Formula III

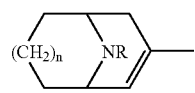

(III)

wherein = represents a single or a double bond; n is 0, 1, 2 or 3; and R represents hydrogen, alkyl, alkenyl, alkynyl, cycloalkyl, cycloalkylalkyl, aryl or aralkyl.

2. The chemical substance of claim 1, which substance is a benzo[b]thiophene of Formula IA

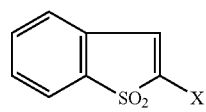

(IA)

a benzo[b]thiazole of Formula IB

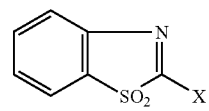

(IB)

a thienopyridine of Formula IC

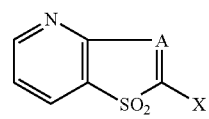

(IC)

a thienopyridine of Formula ID

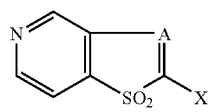

(ID)

a thienopyridine of Formula IE

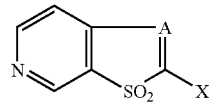

(IE)

or a thienopyridine of Formula IF

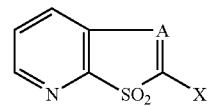

(IF)

wherein A and X are as defined in claim 1.

3. The chemical substance of claim 1, which is a benzo[b]thiophene of Formula IA, wherein X represents a group of Formula III, wherein = represents a double bond;

n is 0 or 1; and

R represents hydrogen, alkyl or aralkyl.

4. The chemical substance of claim 1, which is (±) 3-(2-Benzo[b]thiophenyl-1,1-dioxide)-8-H-8-azabicyclo[3.2.1]oct-2-ene;

(±) 3-(2-Benzo[b]thiophenyl-1,1-dioxide)-8-methyl-8-azabicyclo[3.2.1]oct-2-ene;

(±) 3-(2-Benzo[b]thiophenyl-1,1-dioxide)-8-ethyl-8-azabicyclo[3.2.1]oct-2-ene;

(±) 3-(2-Benzo[b]thiophenyl-1,1-dioxide)-8-allyl-8-azabicyclo[3.2.1]oct-2-ene;

(±) 3-(2-Benzo[b]thiophenyl-1,1-dioxide)-8-benzyl-8-azabicyclo[3.2.1]oct-2-ene;

(±) 3-(2-Benzo[b]thiophenyl-1,1-dioxide)-9-H-9-azabicyclo[3.3.1]non-2-ene;

(±) 3-(2-Benzo[b]thiophenyl-1,1-dioxide)-9-methyl-9-azabicyclo[3.3.1]non-2-ene;

(±) 3-(2-Benzo[b]thiophenyl-1,1-dioxide)-9-ethyl-9-azabicyclo[3.3.1]non-2-ene;

(±) 3-(2-Benzo[b]thiophenyl-1,1-dioxide)-9-benzyl-9-azabicyclo[3.3.1]non-2-ene;

or a pharmaceutically-acceptable addition salt thereof.

5. The chemical substance of claim 1, which is a benzo[b]thiazole of Formula IB, wherein
X represents a group of Formula III, wherein
= represents a double bond;
n is 0 or 1; and
R represents hydrogen, alkyl or aralkyl.

6. The chemical substance of claim 1, which is
(±) 3-(2-Benzo[b]thiazolyl-1,1-dioxide)-8-H-8-azabicyclo[3.2.1]oct-2-ene;

(±) 3-(2-Benzo[b]thiazolyl-1,1-dioxide)-8-methyl-8-azabicyclo[3.2.1]oct-2-ene;

(±) 3-(2-Benzo[b]thiazolyl-1,1-dioxide)-8-ethyl-8-azabicyclo[3.2.1]oct-2-ene;

(±) 3-(2-Benzo[b]thiazolyl-1,1-dioxide)-8-benzyl-8-azabicyclo[3.2.1]oct-2-ene;

(±) 3-(2-Benzo[b]thiazolyl-1,1-dioxide)-9-H-9-azabicyclo[3.3.1]non-2-ene;

(±) 3-(2-Benzo[b]thiazolyl-1,1-dioxide)-9-methyl-9-azabicyclo[3.3.1]non-2-ene;

(±) 3-(2-Benzo[b]thiazolyl-1,1-dioxide)-9-ethyl-9-azabicyclo[3.3.1]non-2-ene; or (±) 3-(2-Benzo[b]thiazolyl-1,1-dioxide)-9-benzyl-9-azabicyclo[3.3.1]non-2-ene;

or a pharmaceutically-acceptable addition salt thereof.

7. The chemical substance of claim 1, which is
(±)3-(2-benzo[b]thiophenyl-1,1-dioxide)-8-H-8-azabicyclo[3.2.1]oct-2-ene.

8. A pharmaceutical composition comprising a therapeutically effective amount of a chemical substance of any of claims 1, 2, 3-6, or 7, any of its enantiomers or any mixture of its enantiomers, or a pharmaceutically-acceptable addition salt thereof, together with at least one pharmaceutically-acceptable carrier or diluent.

9. A method of the treatment or alleviation of pain of a living animal body, including a human, which method comprises the step of administering to such a living animal body, including a human, in need thereof a therapeutically effective amount of a chemical substance of any of claims 1, 2, 3-6 or 7, any of its enantiomers or any mixture of its enantiomers, or a pharmaceutically-acceptable addition salt thereof.

10. The method of claim 9, wherein the disease, disorder or condition is mild, moderate or even severe pain of acute, chronic or recurrent character, as well as pain caused by migraine, postoperative pain, and phantom limb pain.

* * * * *